United States Patent [19]
Jespers et al.

[11] Patent Number: 6,017,732
[45] Date of Patent: Jan. 25, 2000

[54] BACTERIOPHAGE LIBRARY DISPLAYING IMMUNOGLOBULIN REPERTOIRES WITH A CHEMICAL MOIETY COVALENTLY BOUND WITHIN THE BINDING SITE: PRODUCTION AND SELECTION THEREOF

[75] Inventors: Laurent Stephane Anne Therese Jespers, Tervuren, Belgium; Gregory Paul Winter, Cambridge, United Kingdom; Timothy Peter Bonnert, Seattle, Wash.; Thomas Martin Simon, Bad Krozingen-Hausen, Germany

[73] Assignee: Medical Research Council, London, United Kingdom

[21] Appl. No.: 08/564,207
[22] PCT Filed: Jun. 30, 1994
[86] PCT No.: PCT/GB94/01422
§ 371 Date: Sep. 4, 1997
§ 102(e) Date: Sep. 4, 1997
[87] PCT Pub. No.: WO95/01438
PCT Pub. Date: Jan. 12, 1995

[30] Foreign Application Priority Data

Jun. 30, 1993 [GB] United Kingdom .................... 9313509

[51] Int. Cl.$^7$ .............................. C12N 7/01; C12N 15/13; C07K 16/46; C07K 1/107
[52] U.S. Cl. ........................ 435/69.6; 435/69.1; 435/69.7; 435/71.1; 435/320.1; 435/472; 530/350; 530/402; 530/387.1; 530/387.3
[58] Field of Search ....................... 530/350, 402, 530/387.1, 387.3; 435/69.1, 69.7, 69.6, 71.1, 320.1, 472

[56] References Cited

FOREIGN PATENT DOCUMENTS

WO 92/20791 11/1992 WIPO.

OTHER PUBLICATIONS

Clackson et al., Nature 352:624–628 (1991).
Barbas III et al., Proc. Natl. Acad. Sci. USA 89:4457–4461 (1992).
Staunton et al., Protein Engineering 6(Suppl.):93 (1993).
Pollack et al., Science 242:1038–1040 (1988).

*Primary Examiner*—Johnny F. Railey, II
*Attorney, Agent, or Firm*—Marsha, O'Toole, Gerstein, Murray & Borunl

[57] ABSTRACT

Repertoires of first specific binding pair (sbp) members wherein each first sbp member has a chemical moiety bound covalently at an amino acid residue within the binding site are made and may be displayed at the surface of an organism such as a bacteriophage. Methods of making such repertoires may involve the provision of a population of encoding nucleic acid molecules wherein a codon encoding a selectively or preferentially modifiable amino acid is introduced in the region encoding the binding site, for instance by mutation or gene construction. First sbp member (e.g. antibodies) wherein binding to second sbp member (e.g. antigen) is enhanced in or dependent on the presence of the chemical moiety in the binding site may be selected from the repertoires.

25 Claims, 4 Drawing Sheets

BACTERIOPHAGE LIBRARY DISPLAYING IMMUNOGLOBULIN REPERTOIRES WITH A CHEMICAL MOIETY COVALENTLY BOUND WITHIN THE BINDING SITE: PRODUCTION AND SELECTION THEREOF

This is the U.S. National Phase of International Application No. PCT/GB84/01422, filed Jun. 30, 1994.

The present invention relates to members of specific binding pair (sbp) which comprise a binding site for complementary second sbp member. More particularly, it relates to sbp members, especially repertoires thereof, wherein a chemical moiety is incorporated specifically at an amino acid residue within the binding site. It also relates to the production of such repertoires and selection of such repertoires and selection from a repertoire of first sbp member with binding specificity for a second sbp member of interest. The sbp member may be one wherein the binding site is formed by binding regions of immunoglobulin heavy and light chain variable domains.

It was disclosed in WO 92/01047 that polypeptides which are members of specific binding pairs, including antibody fragments, can be displayed on the surface of bacteriophage and that they will bind complementary members of the specific binding pair, e.g. antigen in the case of antibody. First sbp member with desirable binding properties-can be selected directly using this characteristic. The principles described therein have been subsequently extended in the further patent applications WO 92/20791; WO 93/06213; WO 93/11236 and WO 93/19172. Phage libraries have been prepared displaying antibody repertoires from for instance human peripheral blood lymphocytes and the spleens of immunized animals and specific antibodies isolated. In WO 92/01047, it is described how V gene repertoires for display on bacteriophage may be made in vitro by combining un-rearranged V genes, with D and J segments. Antibodies against a variety of antigens have been selected from such artificially rearranged V gene repertoires displayed on phage (H. R. Hoogenboom & G. Winter J. Mol. Biol. 227 381–388 1992; and as disclosed in WO 93/06213 and WO 93/11236).

However, the chemical diversity of these encoded libraries is restricted to natural amino acids. It would be desirable to be able to incorporate other reactive groups at the binding site of sbp members such as antibodies. These would have a number of applications.

The development of antibody based biosensors (reviewed by J. R. North, Trends Biotechnol. 3 180–186, 1985) has been limited by the ability to combine recognition and effector functions into the same molecule. Transduction of the antigen binding event would need to be mediated by alternative means such as fluorophores, luminophores or redox groups. These reporter groups should ideally be an integral part of the antibody binding site, such that antigen binding would lead to a change in the groups microenvironment, and a corresponding change in the fluorescence, luminescence or redox potential.

Similarly, the design of catalytic antibodies (reviewed by R. A. Lerner et al. *Science* 252 659–667, 1991) would be facilitated by the incorporation of nucleophilic groups and non-peptidyl cofactors such as metal ions, haems and flavins, a common feature of many enzymes, into the antibody binding site. These modifying groups would ideally be incorporated covalently at the antigen binding site, thus becoming integral parts of the paratope. Such chemically modified antibodies could then be used directly as detection agents in immunoassay applications, such as time resolved fluorescence immunoassay, or directly in catalysis.

In this application, we demonstrate that chemical groups can be covalently incorporated into a repertoire of sbp members displayed on phage and that sbp members can be selected from these repertoires with covalently bound groups at the antigen binding site. We have called such repertoires, chemisynthetic libraries.

The utility of the incorporation of chemical moieties at the antigen binding sites of antibody molecules has been recognized by previous workers, particularly for the derivation of catalytic antibodies. Rational protein engineering has been used (V. A. Roberts et al, Proc. Natl. Acad. Sci. 87 6654–6658 1990; B. L. Iversen et al Science 249 659–662, 1990; D. G. Gregory et al, Protein Engineering 6 29–35, 1993) where metal coordination sites were designed to chelate metal ions into the antigen binding site, for example at the light chain complementary determining regions. Roberts et al suggest that the combination of a specific light chain or heavy chain containing a catalytic metal site with a library of complementary chains raised to potential substrates or transition state analogues should improve the isolation of catalytic antibodies with desired activities and specificities. Gregory et al report that a zinc binding site has been incorporated by design in to the anti-lysozyme antibody HyHEL5 and both antigen binding and metal chelation retained.

C. F. Barbas et al (Proc. Natl. Acad. Sci. USA 90 6385–6389, 1993; published July 1993) have proposed the use of an iterative strategy involving random mutagenesis and selection for the isolation of catalytic antibodies. The authors propose that CDR mutagenesis to create a metal binding site is followed by mutagenesis of other CDRs to generate catalytic metalloantibodies that bind both metal and a hapten.

Barbas et al started with a preexisting antibody Fab fragment with specificity for tetanus toxoid which they mutagenized and displayed on phage and selected from the libraries Fab fragments which bind to metal. They then propose diversifying the isolated metal binding Fab fragments, by chain shuffling or by mutagenesis of another CDR, and then selecting to obtain specificity for the substrate but have not as yet reported whether this can be accomplished successfully. In Example 2 we describe the construction of a library of scFv fragments prepared synthetically from human V genes can be made where the antigen binding sites contain an amino acid residue which may be specifically modified to introduce a functional group. The residue is specifically chemically derivatized before every selection process so that antibody fragments are identified which bind to antigen, with a non-protein element incorporated at the antigen binding site.

Ward et al, *Nature* 341: 544–546, 1989, suggested the concept of Fv fragments in which the VH domain binds substrate and side chains or prosthetic groups in the $V_K$ domain stabilize the transition state or attack the substrate.

It is demonstrated in this application that sbp members (eg antibody fragments) can be obtained which are dependent on derivatization to bind strongly to complementary sbp member (eg antigen). Earlier work on metalloantibodies envisaged that the metal would not be involved in the primary recognition of antigen (Roberts et al, 1990 supra; Gregory et al, 1993 supra). No antibody fragment has yet been isolated by other workers where the recognition of antigen is absolutely dependent on the presence of metal at the antigen binding site.

The present invention provides a novel approach to the obtention of first spb members with a binding site for second sbp member, ameliorating problems or difficulties associated with the prior art.

Herein, unless the context requires otherwise, reference to "antibody" or "antibody fragment" means a first sbp member which has its binding site formed by association of a first polypeptide domain which comprises a binding region of an immunoglobulin heavy chain variable domain (VH) and a second polypeptide domain which comprises a binding region of an immunoglobulin light chain variable domain (VL) and includes the Fab fragment consisting of VL, VH, CL and CH1 domains, the Fv fragment consisting of the VL and VH domains of a single antibody, single chain Fv (scFv) comprising a VL domain and a VH domain linked by a peptide linker, F(ab')2 fragments, a bivalent fragment comprising two linked Fab fragments, bispecific single chain Fv dimers (PCT/US92/09965) and diabodies, bivalent or bispecific fragments constructed by gene fusion (P. Holliger et al, supra; PCT/GB93/02492).

The term "repertoire" is used to indicate diversity, ie variety in sequence, and generally implies a large number of different sequences, perhaps of the order of millions (eg $10^7$–$10^9$–$10^{12}$–$10^{14}$). A repertoire of antibodies or antibody fragments may have a diversity which is representative of that found in an organism such as mouse or human. One would expect to be able to isolate from a repertoire of first sbp members a large number of different first sbp members each able to bind one of a wide variety of different second sbp members.

The invention provides a repertoire, which is genetically diverse, of first sbp members each having a binding site which comprises a chemical moiety bound covalently at one or more amino acid residues within the binding site. The chemical moiety is not encoded by nucleic acid used to express the first sbp members, instead being introduced by a covalent modification following production of the polypeptides. One or more first sbp members with binding specificity for a second sbp member (antigen) of interest may be selected from the repertoire, e.g. employing binding affinity. Of particular interest and advantage is the ability to select first sbp members whose binding to second sbp member of interest is enhanced by the presence of the chemical moiety, or even dependent entirely on it. A chemically modified sbp member may bind second sbp member of interest with greater affinity than unmodified, genetically identical sbp member when binding is compared under the same conditions. Also, there may be no binding at all in some cases without the chemical moiety being covalently bound within the binding site of the first sbp member. Then, the chemical moiety forms an integral part of the binding site, being essential for the second sbp member (antigen in the case of antibody) to form non-covalent bonds with it to obtain high affinity binding.

The chemical moiety is introduced at a specific chemically modifiable residue or residues. A chemically modifiable amino acid residue is an amino acid residue susceptible to modification with a chosen chemical reagent under specified conditions. The amino acid may be unique in the binding site, or it may be uniquely modifiable, or selectively or preferentially modifiable over other amino acids present. For instance, a cysteine residue may be introduced into the binding site and be available for chemical modification via its thiol group. There may be other cysteines in the molecule (eg in a VH domain) but generally those would be paired by disulfide bridges and so not available for chemical modification, or at least not so available as the one introduced into the binding site which is therefore selectively or preferentially modifiable. It may also be possible to render an amino acid preferentially modifiable compared with other amino acids of the same type within the sbp member by engineering its environment, eg by positioning it within the molecule adjacent another amino acid with particular properties. For instance, an amino group next to a carboxlate group would be rendered more nucleophilic and selectively modifiable even if not unique within the binding site.

The repertoire may contain a unique amino acid in each first sbp member, an amino acid which is uniquely modifiable in each first sbp member or more than one preferentially modifiable amino acid residue in each first sbp member. The repertoire needs to be modifiable reproducibly at one or more specific amino acid residues to that reproducible modification may be made of selected repertoires and of polypeptides expressed from clones selected from a repertoire.

There are several additional features of the present invention which differ from the prior art. The chemical moiety is incorporated at the site covalently and may form a critical determinant of the binding site. This covalent modification allows a wider variety of moieties to be incorporated, particularly reporter groups or cofactors for catalysis. In one embodiment of the present invention, one or more amino acids which are specifically modifiable are incorporated at the binding site. This allows the interaction of large organic groups such as the fluorescent reporter group, 7-nitrobenz-2-oxa-1,3-diazole (NBD) for the first time. Other large groups such as the flavin cofactors for catalysis, FMN and FAD may be incorporated. There is no previous example where a whole repertoire of binding proteins has been derivatized and binders isolated. Significantly, for the first time a scFv fragment (encoded by clone SSL-34, example 2) has been isolated which requires derivatization with a non-protein element to obtain detectable binding to antigen.

The incorporation of a covalent modification to generate a chemisynthetic repertoire involves a number of difficulties. First, there needs to be an amino acid residue in the binding site which can be specifically modified with a reagent to give a dervatized antibody. Secondly, introduction of a chemical moiety into a binding protein, such as antibody, with pre-existing binding proteins is likely to cause alterations in the properties of binding. Modification at a site outside the binding site is likely to make the introduced group much less useful as a reporter or catalytic group. The present invention overcomes these difficulties by allowing selection of binding proteins ("first sbp members") which can bind second sbp member of interest when the introduced group is present in the binding site. Many of the binding proteins (eg antibodies) only bind the target of interest (eg antigen), or show greatly improved binding, when chemically modified. This differs from previous approaches involving modification of a single antibody known, initially, to bind the antigen of interest.

Since, in the invention, the chemical group is present in the binding site, its properties are more likely to be modified by binding of antigen. This makes the method a powerful one for incorporation of reporter groups such as fluorescent groups for immunoassay, since the properties of these groups are much more likely to change if they are close to the site where antibody binds. Cofactors for catalysis will also need to be close to where substrate binds in catalytic antibodies. One embodiment of this would be to provide the cofactor on a fixed light chain and select heavy chains which supply substrate specificity. Groups may be incorporated at the antigen binding site which favour high affinity binding of the antigen or promote a particular selectivity of binding for instance to discriminate between antigen molecules of different sizes. The in vitro generation of binding modules allows the in vitro modification of these structures to include non-peptidyl elements.

Although synthetic moieties could be engineered via disulfide linkage at any accessible surface exposed cysteine residue, the antigen binding CDR regions are the obvious targets for modification. Modification of the light chain CDR3, should result in the synthetic element forming an integral part of the binding site and yet still permit antigen contacts to be formed by the dominant heavy chain CDR3. The diversity and functionality of antibodies might therefore be increased beyond that possible with existing antibody libraries by inclusion of these non-encoded elements.

The methods described in this application will allow virtually any chemical moiety to be incorporated into the binding site and be an essential component for efficient binding activity. The first sbp members in the repertoire may be fused to a surface component of any organism for display at the surface. In chemisynthetic libraries displayed on filamentous bacteriophage, each clone expresses a first sbp member as a fusion protein on the phage surface by inserting the corresponding gene into the gene coding for a surface component such as the cpIII viral coat protein. Nucleic acid encoding the binding protein displayed on the surface of an organism may be packaged within the organism for easy recovery following selection of first sbp member able to bind second sbp member of interest.

Selection of a first sbp member from a repertoire is preferably by binding with second sbp member of interest.

Following selection of a first sbp member displayed at the surface of an organism which contains a nucleic acid molecule which encodes the first sbp member, the nucleic acid may be recovered from the organism and used, or other nucleic acid molecules with the same sequence, or other nucleic acid molecules encoding the same amino acid sequence, or a mutant or derivative thereof, used in the production of first sbp member with a binding site able to bind the second sbp member of interest.

Individual first sbp members with the desired specificity eg for an antigen, can be isolated from the complex library using the conventional screening techniques (e.g. as described in Harlow, E., and Lane, D., 1988, supra Gherardi, E et al. 1990. *J. Immunol. meth.* 126 p61–68).

Selection will often be elution from an affinity matrix with a ligand. Elution with increasing concentrations of ligand should elute displayed binding molecules of increasing affinity.

An affinity matrix which has retained the strongly bound first sbp member displayed on the surface of an organism and extract the DNA, for example by boiling in SDS solution. Extracted DNA can then be used directly to transform *E. coli* host cells or alternatively the encoding sequences can be amplified, for example using PCR with suitable primers, and then inserted into a vector for expression.

If one wishes to select from a population of phages displaying a protein molecule with a high affinity for its ligand, a preferred strategy is to bind a population of phage to an affinity matrix which contains a low amount of ligand. There is competition between phage, displaying high affinity and low affinity proteins, for binding to the ligand on the matrix. Phage displaying high affinity protein is preferentially bound and low affinity protein is washed away. The high affinity protein is then recovered by elution with the ligand or by other procedures which elute the phage from the affinity matrix.

In summary then, for recovery of the packaged DNA from the affinity step, the package can be simply eluted, it can be eluted in the presence of a homologous sbp member which competes with said package for binding to a complementary sbp member; it could be removed by boiling, it could be removed by proteolytic cleavage of the protein; and other methods will be apparent to those skilled in the art eg. destroying the link between the substrate and complementary sbp member to release said packaged DNA and sbp member. At any rate, the objective is to obtain the DNA from the package so that it can be used directly or indirectly, to express the sbp member encoded thereby.

As discussed elsewhere, binding of the selected first sbp member to the second sbp member may be enhanced compared with binding of the same first sbp member without the chemical moiety covalently bound at an amino acid (one or more) in the binding site. The binding may be dependent on the presence of the chemical moiety.

A method of providing a diverse repertoire of a first specific binding pair (sbp) member according to the present invention comprises a step of chemical modification of first sbp members to introduce a chemical moiety bound covalently to an amino acid residue in the binding site of each first sbp member. Provision of the repertoire of first sbp member before the step of chemical modification may comprise expression from a population of nucleic acid molecules collectively encoding the repertoire. Provision of the population of nucleic acid molecules may comprise a step of mutation of nucleic acid encoding first sbp member, or a polypeptide component part thereof (eg one polypeptide chain of a heterodimeric binder such as a Fab fragment), to introduce a codon encoding the amino acid residue. Equally, the nucleic acid may be constructed by joining together, eg in a combinatorial fashion, of gene fragments. These may be done using PCR.

One approach aims at creating a semisynthetic library on phage by the covalent incorporation of synthetic moieties on to the whole phage-binding protein population prior to each selection step. Semisynthetic phage-antibodies isolated with binding activity are shown to tolerate or even to require the presence of the synthetic group into their antigen-binding sites. In the latter case, these antibody fragments may be the best candidates for use in single phase immunoassays and catalysis. In example 1 we report how we tested the reactivity of a unique cysteine free thiol functionality in the light chain CDR3 of a scFv expressed as a soluble protein or as a fusion product to filamentous phage. Having assessed the specificity of the semisynthesis, we then in example 2 selected semisynthetic scFv's activities against phOx with two different synthetic moieties, using disulfide exchange or alkylation reaction. By repeating this chemical modification on a scFv library before each selection step against the hapten 2-phenyloxazol-5-one (phOx) conjugated to a carrier, we have found that several clones eluted after four rounds of selection require the presence of the covalently bound moiety to produce an enhanced ELISA signal against the antigen. One clone selected with the 7-nitrobenz-2-oxa-1,3 diazole (NBD) fluorophore was further characterized: a much higher ELISA signal was obtained with antigen when the fluorophore was incorporated into the antigen binding site.

The examples describe the use of a single chemically modified light chain in combination with a repertoire of heavy chains. This would be readily extendable to incorporation of groups in a repertoire of different light chains or heavy chains in a synthetic repertoire displayed on phage. Although the simplest position to incorporate cysteines is the CDR3 of the heavy or light chain, they could in principle be incorporated at any position in the chains using mutagenesis or joining together of gene fragments. Although cysteine may be present elsewhere in a VH domain they may form disulfide bonds and not be available for chemical modification.

Refinements may be made of the above basic system. The group introduced may be linked to the displayed binding protein by a cleavable group such as a disulfide bond or a vicinal diol. During selection of phage with the introduced group in the binding site, phage may then be eluted from complementary second sbp member using the cleavage reagent. Those phage where binding is dependent on the present of the introduced group should be preferentially eluted, whereas those whose binding is independent will be retained.

The linker length between the introduced group and the binding site may be varied. This allows the exploration of the space of the binding site to find the position of the introduced group which best allows it to fulfill its function as, for instance, a reporter or a catalytic group.

Cysteine groups may be introduced at more than one site on the molecule, for example at different CDR residues in an antibody or antibody fragment. Modification may be performed for instance on both heavy and light chains allowing derivatization with two introduced groups. Cysteines may be introduced at specific points within varying CDRs by incorporating cysteine encoding codons, for instance at specific positions within random oligonucleotides. Even if in some fragments this leads to derivatization at more than one site, selection by binding to antigen will allow those fragments where derivatization is compatible with binding to be selected. There is also the possibility of incorporating two (or more) residues for modification with the same reagent or two (or more) different reagents, or more preferably different residues may be modified with different reagents to incorporate different chemical moieties into the binding site. This is useful eg for catalytic antibodies where the presence of two chemical moieties such as flavin and haem may promote catalysis of a redox reaction.

In a further embodiment, the modification may be performed on a protein chain, e.g. light chain, in solution, eg using the procedures described by M. Figini et al., *J. Mol. Biol.* 239, 68–78, 1994. The light chain may be then associated with a population of heavy chains on phage and antigen binders selected. This association would be repeated at each round of selection prior to contacting the phage population with the antigen.

The present invention provides a novel way of introducing metal ions at the binding site of a first member of a specific binding pair. Chelating groups such as iminodiacetic acid may be incorporated at the binding site e.g. at a cysteine residue, and then a metal containing solution added. The use of a spacer arm would give greater flexibility for the positioning of the metal ion for catalysis compared to the use of amino acid residues directly for chelation as other workers (Roberts et al, 1990 supra; Gregory et al, 1993; Barbas et al, 1993) have done.

There are other possible ways of modifying the binding site of polypeptides. There are a number of amino acid residues which may be specifically derivatized using molecules containing specific functional groups. For instance, amino groups may be modified with N-hydroxysuccinimide esters, carboxyl groups with carbodiimides, histidines and cysteines with halomethyl ketones, arginine with glyoxals (see e.g. A. R. Fersht, Enzyme Structure and Mechanism 2nd edn, 1985 pp248–251, W. H. Freeman, New York). The problem with modification of these residues is how to modify those at the binding site since they may be present at other sites. In many cases it may be possible to modify those which are not at the binding site without affecting activity. This has been a common method of determining which amino acid residues are at the catalytic site of enzymes (Fersht et al, 1985 supra), since only modification of these sites affects activity.

Some reagents which may be used to modify specific amino-acid residues are given by T. Imoto and H. Yamada in "Protein Function: a Practical Approach", pp247–277, 1989. To introduce specific functional groups into polypeptides the reactive group of these reagents may be combined with the functional group in a modifying reagent. For instance, if it is desired to modify a protein with the fluorophore 7-amino-4-methylcoumarin-3acetic acid, the N-hydroxysuccinimidyl ester of the molecule may be used to modify amino groups, whereas N-[6-(-amino-4-methylcoumarin-3-acetamido)hexyl]-3'-(2'-pyridyldithio)propionamide may be used to modify cysteine groups.

Specific modification at an antigen binding site of residues which are found more commonly than cysteine, such as lysine, glutamate, histidine or tyrosine, may be achieved by using mutated synthetic segments, such as V genes, to construct the library. For example, if it is desired to modify specifically a lysine in CDR3 of the heavy chain, the library may be constructed from gene segments of VH and VL domains where all lysine residues have been mutated to another amino acid such as arginine. The lysine in VH CDR3 may then be specifically chemically modified.

Another possible methodology is to use transglutaminase which catalyzes an acyl-transfer reaction between the gamma-carboxyamide group of glutamine residues and primary amines (E. Bendixen et al, J. Biol. Chem. 26821962–21967, 1993; K. N. Lee et al *Biochim. Biophys. Acta* 1202 1–6 1993; T. Kanaji et al *J. Biol. Chem.* 268 11565–11572 1993). This enzyme could therefore introduce amino acid residues from a peptide into a glutamine residue at the binding site through a peptide lysine epsilon amino group or into a lysine group at the antigen binding site via a peptide glutamine group. The enzyme could also catalyzed derivatization of binding site glutamine residues with a primary amine. Again, since, glutamine residues and lysine residues are common in antibodies, it would be advantageous-to construct the library from gene segments where these residues had been mutated to other residues except for those where modification was desired.

A further approach is to introduce chemical moieties to either the N or C terminus of polypeptides displayed on phage using reverse proteolysis or chemical conjugation or a combination of the two (I. Fisch et al, *Bioconj. Chem.* 3, 147–153, 1992; H. F. Gaertner et al, *Bioconjug. Chem.* 3, 262–268, 1992; H. F. Gaertner et al, *J. Biol. Chem.* 269, 7224–7230, 1994; J. Bongers et al, *Biochim. Biophys. Acta,* 50, S57–162, 1991; R. Offord, *Protein Engineering,* 4, 709–710, 1991). These methods have been used to introduce non-encoded elements to protein and peptide molecules. The use of these methods to derivatize repertoires may be particularly valuable for selection of enzymes and receptor binding peptides which bind substrate or receptor only when modified with the chemical moiety.

Examples of fluorophores which may be introduced are fluorescein, phycoerythrin, coumarin, NBD, Texas Red and chelated lanthanide ions. Examples of catalytic groups which may be introduced are flavin adenine dinucleotide (FAD), flavin mononucleotide (FMN), cytochromes and chelated metal ions such as zinc and copper.

This application demonstrates that chemical elements can be incorporated into libraries displayed on phage to increase diversity of displayed libraries above that which can be obtained by genetic encoding. This may expand the scope of protein engineering of both antibodies and other proteins, such as enzymes, where non-protein groups promoting catalysis may be incorporated, or receptor molecules.

Other aspects of the invention and modifications will be apparent to those skilled in the art. Embodiments of the present invention will now be exemplified with reference to the figures.

Figure 5:
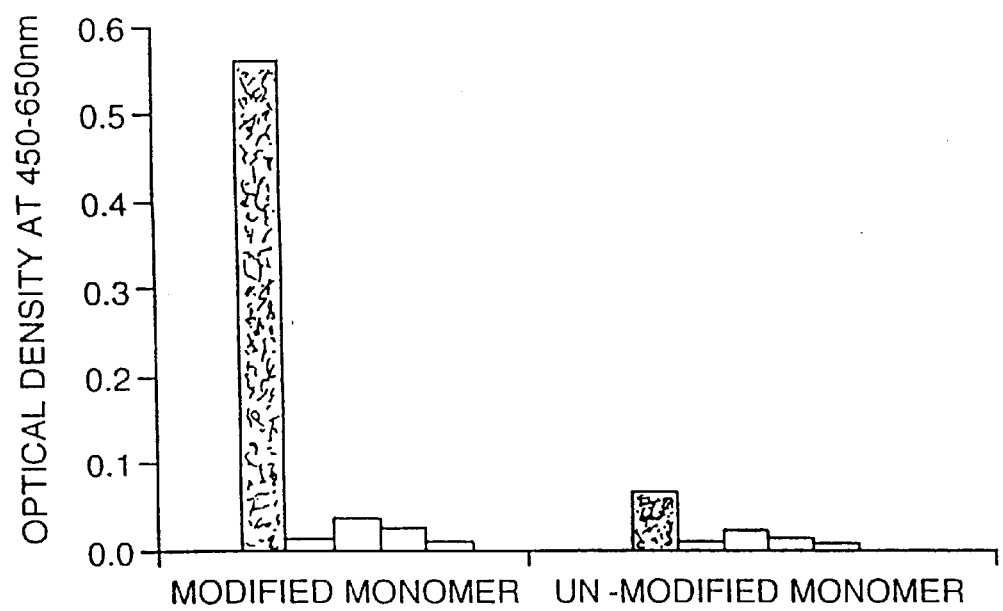

FIG. 5 shows the specificity of soluble scFv fragments derived from clone SSL-34 as determined by the ELISA signal obtained. Soluble scFv fragments were purified by FPLC gel filtration on Superdex 75 to given monomeric fragments and modified with IA-NBD (left hand plots) or left unmodified (right hand plots). The antigens are (left to right) phOx-BSA (black bar), phoxCSA, phOx-KLH and phOx-polylysine, BSA.

All documents mentioned in the text are incorporated herein by reference.

EXAMPLE 1 INTRODUCTION AND MODIFICATION OF A CYSTEINE THIOL AT THE ANTIGEN BINDING SITE OF A MODEL ANTI-NIP ANTIBODY.

The work described in this example shows that a cysteine thiol can be incorporated at the binding site of an antibody molecule and specifically modified to introduce a chemical group.

Among the amino acid side chains, the cysteinyl thiol is generally the most nucleophilic group and hence a valuable candidate for a mild site-specific derivatization via disulfide exchange or by alkylation. In the absence of denaturants, the internal cysteines of antibody fragments form disulfide bridges which are resistant to reduction by 20 mM DTT at room temperature. Therefore, the introduction of a surface-accessible cysteine by site-direction mutagenesis is likely to produce an antibody fragment bearing a unique thiol for modification. We assumed that the internal cysteines will not also react and perturb the folding pathway. The major coat protein, cpVIII, lacks cysteinyl residues but the minor coat protein, cpIII, to which the scFv is genetically fused, contains 8 cysteines equally distributed in the two postulated domains. Although it was hoped that these cysteines formed disulphide bonds it was not known whether they would be reactive or whether modification would compromise the infectivity of the phage.

We chose to carry out initial studies with the NIP12 scFv as a model. Methods used were as follows:

Construction of a Cys-Containing Version of pHEN1-Vλ.

The Ser93 residue of the Vλ3 light chain variable domain encoded in the pHEN1-Vλ3 vector was converted into a Cys residue by in vitro mutagenesis (Amersham International) using the primer 5'-ACC ACT GCT GTC CCG GCA GTT ACA GTC ATA GTC-3'. This new vector was called pHEN1-Vλ-C93.

Construction of a Cys-Containing Version of NIP12 SCFV.

The NIP12 heavy chain variable domain was excised as a NcoI-XhoI fragment from the corresponding clone that was affinity selected against the 3-iodo-4-hydroxy5-nitrophenylacetate hapten (NIP). This NIP12 clone derives from a library wherein 49 human VH germline sequences were linked by PCR to a synthetic library of randomized CDR3 (of length 5 and 8) and cloned into the pHEN1-Vλ phagemid vector (Hoogenboom & Winter, J. Mol. Biol. 227 381–388 1992). The NIP12 heavy chain fragment was then recloned into the corresponding sites of pHEN1-Vλ3-C93 for soluble expression of NIP12-C93 scFv, a protein identical to the NIP12 scFv except that it carries the engineered cysteine residue at position 93 in the Vλ3 light chain.

For phage display of the NIP12 scFv and its cysteine mutant, we separately recloned the two genes as SfiI-NotI fragments into the corresponding sites of the fd-Tet-SfiINotI phage vector. We have chosen the multivalent display fd vector rather than the monovalent display pHEN 1 phagemid, to facilitate the Western-blot analysis of phage proteins. Indeed, the percentage of cpIII-fused scFv rises to approximately 90% with the fd vector whereas it does not exceed lot with the pHEN1 phagemid.

The NIP-binding antibody fragment was isolated by affinity-section as described by Hoogenboom & Winter (1992; supra). It comes from a scFv library assembled by the linkage of a single human Vλ3 light chain to a synthetic repertoire of human germline VH genes rearranged in vitro. As the light variable domain is kept constant in the library, the cysteinyl residue was introduced into this segment. Since CDR3 of the light chain usually forms a larger part then CDR1 and CDR2 of the antigen-binding site, we decided to mutate the L-CDR3 serine 93 into a cysteine. As the CDR3 of both Vλ3 Kol light chain encompasses 10 residues, we postulated on the basis of the spatial conformation of the Kol LCDR3, that the side chain of residue 93 will lie perpendicular to the binding cleft and be solvent-accessible.

Both NIP12 and its mutant NIP12-C93 scFv were prepared. The gene of the latter as assembled by excising from the pHEN1-Vλ3 cloning vector by NcoI-XhoI digestion and recloning it into the corresponding sites of pHEN1-Vλ3-C93 (same vector as pHEN1-Vλ3 with the Ser93 to Cys93 mutation in the light chain Vλ3 introduced by site directed-mutagenesis). The yields of purified protein were similar for the two clones (about 1.5 mg per culture liter) as were their retention times on Superdex G-75 column. The soluble ELISA signal on NIP-coated plate was slightly less intense for the mutant protein than for NIP12. Thus, the introduction of a fifth cysteine into a scFv is tolerated.

The solvent-accessibility of the engineered thiol was then tested by a chemical modification analogous to that used in libraries. The incubation with a large excess of $^{14}$C-iodoacetamide at a 70:1 molar ration (iodoacetamide:scFv) was preceded by a reduction step with DTT (DTT:scFv molar ratio of 7:1) to release the putative fraction of blocked cysteinyl 93 residues. NIP12-C93 scFv incorporated $^{14}$C-iodoacetamide whereas almost no radioactivity was-incorporated into the control protein (NIP12). Similar results were obtained with bulkier alkylating reagents bearing either fluorescein (IA-F) or 7-nitrobenz-2-oxa-1,3 diazole (IA-NBD). To evaluate the completion of the modification, the NIP12-C93 scFv modified with IA-F was analyzed on a 12% polyacrylamide native get (35 mM HEPES, 43 mM Imidazole, pH 7.50). As fluorescein carries one negative charge at pH 7.50, unmodified and modified proteins migrate at different rate towards the anode. The reaction reaches completion within 2 hours.

When displayed on phage, the cpIII-fused NIP12 and NIP12-C93 are equally expressed as detected by Wester blots using antiserum against gene III protein. As similar phage titers are observed, we concluded that the presence of an extra cysteine on the phage surface do not affect its morphogenesis and infectivity. Also, the phage-ELISA signals were in accordance with the soluble ELISA results mentioned above.

Because of their insolubility at higher concentration, phage particles usually do not exceed $10^{12}$ TU (for fd vector) to $10^{13}$ TU (for phagemid) per ml. In comparison to the soluble scFv concentration used for modification (±5 $\mu$M). cpIII-fused scFv are thus considerably less concentrated (±2 nM for both fd phage and phagemid since the latter packages only 10% of cpIII-fused scFv). Therefore, we also decided to lower the concentration of modification reagent down to 30 $\mu$M. This is still a large excess (about 1.5 $10^4$ times) but, as the reacting groups (iodoacetamide and disulfide exchanger) are thiol-specific, it enabled us to limit the reaction to two hours. This specificity of semisynthesis on phage-antibody was demonstrated in the following experiment: 1 ml fd phage stocks displaying either the NIP12 scFv or NIP12-C93 were first incubated in reducing conditions (1 mM DTT for 30 min) then precipitated twice-to remove any traces of DTT and finally reacted with 30 $\mu$M iodoacetyl-LC-biotin for 2 hours at 4° C. Western blot analysis showed that the modifying reagent was markedly more incorporated into the cpIII-fused NIP12-C93 protein but the extent of the reaction could not be estimated with accuracy. It was also shown that the reaction conditions do not alter the phage infectivity, a crucial observation with regard to the semi-synthetic phage-antibody selection (data not shown).

EXAMPLE 2 GENERATION OF A CHEMISYNTHETIC ANTIBODY REPERTOIRE AND SELECTION OF ANTIBODIES BINDING TO 2-PHENYLOXAZOL-5-ONE.

In the work described in this example, a chemisynthetic library was prepared with a fixed light chain and a repertoire of heavy chains and antibodies specific for 2-phenyloxazol-5-one then selected.

As introduction of the chemical group on phage was proven to be site-specific, we tested whether binding activities displayed on phage could be selected on the basis of their non-encoded chemical diversity.

93In this method each selection step is preceded by semisynthesis on the whole phage-antibody library amplified after the previous selection round.

First, the same library as described by Hoogenboom & Winter (1992; supra) was constructed except for the serine 93 to cysteine 93 mutation in the light chain V$\lambda$3 variable domains. Briefly, we excised the synthetic VH library cloned into pHEN1-V$\lambda$3 by NcoI-XhoI digestion and recloned it into the same sites of pHEN1-V$\lambda$3-C93. After electroporation of E. coli TG1 with the ligated DNA, a library of 2.6×10$^7$ clones was obtained wherein greater than 83% of the clones had insert. Methods used in this section are described below.

Construction of a Cys-Containing Synthetic Library.

The two unselected synthetic libraries (1.0×10$^7$ combinations each) described in Hoogenboom & Winter (1992; supra) were mixed and CsC1-grade plasmid DNA was prepared. By NcoI-XhoI digestion, the synthetic heavy chain library fragment was excised from this DNA, purified on agarose gel and ligated into the pHEN1-V$\lambda$3-C93 expression vector prealably cut with NcoI and XhoI. The ligated DNA was then purified by GeneClean (Biolol) and electroporated into E.coli TG1. A library of 2.6 $10^7$ clones were obtained wherein greater than 831; of the clones had insert.

Preparation of Semisynthetic Phage-Antibodies.

a. Phage-antibody culture: in 50 ml 2XTY-Amp-Glu1%, phagemid particles were rescued from the exponentially growing library by superinfection at 37° C. for 30 min with VCSM13 helper phage (at a ratio of 20 phage units per cell). Cells were then spun down (4K rpm for 15 min) and resuspended in 250 ml of prewarmed (37° C.) 2XTY-Amp-Kan medium. After incubation for 1 hour at 37° C. with shaking, the culture was grown for 16–18 hours at 30° C. with shaking. For scFv cloned into fd vector, 250 ml of 2XTY-Tet were inoculated with 100 $\mu$l of an overnight culture and grown for about 20 hours at 30° C.

b. Phage-antibody purification: after the removal of the cells (7K rpm for 25 min). the phage particles were concentrated by a first PEG/NaC1 precipitation (7K rpm for 25 min) and resuspended in 5 ml of a fresh and degassed 1 mM DTT solution. This step ensures that all cysteines 93 blocked by SH-containing molecules are now released for temperature, the phage were PEG/NaCl precipitated (4K rpm for 15 min) and the phage pellet was carefully washed twice with 1 ml of degassed reaction buffer (10 mM phosphate, 10 mM EDTA, pH 7.80) before resuspension in 5 ml of the same buffer. A third PEG/NaCl precipitation followed by two washes with reaction buffer was introduced to remove the remaining traces of DTT. The final pellet (approximately 1.0 to 3.0 $10^{13}$ TU) was then resuspended in 1–2 ml of degassed reaction buffer.

c. Senisynthesis on phage-antibody: 1.6 mM solutions of synthetic moieties were freshly prepared in dimethylformamide (DMF) for the iodoacetyl-LC-biotin (Pierce), iodoacetamide-NBD (IA-NBD) and iodoacetamide-fluorescein (IA-F) probes (Molecular Probes) or in reaction buffer for the 2-pyridyl-dithio-ethyleneamine (PDEA) agent (Pharmacia Biosensor). 20 $\mu$l of synthetic moiety was then mixed with 1 ml concentrated phage-antibody stock and the reaction mixture was kept for 2 hours at 4° C. in the dark. The reaction was then quenched for 1 hour at room temperature by adding 2 $\mu$l of a fresh 0.1M DTT solution. Before selection or ELISA test, the quenched reactant in excess was not removed by PEG/NACl-precipitation of the phage particles.

Selection of Semisynthetic Phage-Antibodies

For selection, the protocol described in Marks et al (J. Mol, Biol. 222 581–597 1991) was followed except that a 100 $\mu$g/ml phOx-BSA solution in PBS was used for coating the immuno tubes (Nunc Maxisorp) and all phage-antibody incubations were performed in the dark at room temperature. Four rounds of selection-rescue were done. to elicit phOx-binders.

Preparation of Semisynthetic scFvs.

a. ScFv culture: the protocol described by Marks et al (1991; supra) was followed.

b. ScFv purification: as the three scFv to purify contained human VH3 domains (NIP12, NIP12-C93 and OXs32), the protocol described by Hoogenboom & Winter (1992; supra) was followed. Monomeric scFv fractions were purified by gel filtration on a Superdex 75 column ((Pharmacia) and stored at 4° C. in PBS, 0.02%; NaN3 until modification.

c. Semisynthesis on ScFv: the modification protocol started by reducing the blocked cysteines 93: the scFv (100 μg in 600 μl of degassed reaction buffer) was incubated with, 10.4 μl of a fresh 2.5 mM DTT solution in degassed reaction buffer (DTT:scFv molar ratio of 7:1). The reaction mixture was kept at room temperature. Meanwhile, 3.5mM solutions of modification reagent were freshly prepared in degassed reaction buffer for $^{14}$C-iodoacetamide (4.3 μM/ml, 0.25 mCi/ml, Amersham) or in DMF for the IA-NBD and IA-F fluorescent reporters. After 1.5 hour reduction, 75 μl of these modification solutions (reagent:scFv molar ratio of 70:1) were added to reaction mixture which was then incubated at 4° C. for 2 hours in the dark. The reaction was then quenched with 5.2 μl of a fresh 0.25 M DTT solution (DTT: reagent molar ratio of 5:1). The completion of the reaction (+1 hour at room temperature) was followed by TLC with CHCl$_3$:CH$_3$OH 9:1 as eluant. Until use, the semisynthetic scFv solution was kept at 4° C. in the dark.

For fluorescence analysis, it was necessary to remove most of the quenched reagent. Therefore, the reaction mixture was purified by gel filtration on G-25 Sephadex fine (9 ml bed volume) equilibrated with PBS. The semisynthetic scFv was collected in 2 ml and used as such for fluorescence titration.

Semisynthetic Phage-Antibody and ScFv ELISA.

Semisynthetic phage-antibody stocks were first 100-fold diluted before ELISA analysis as described by Clackson et al (1991). Semisynthetic scFv ELISA were done according to Marks et al (1991;supra). For the unmodified clones, the purified phage particles or scFv were mixed with an excess of DTT-quenched reactant before analysis. ELISA plates were coated with a 100 μg/ml phOx-BSA solution in PBS overnight at room temperature. For specificity ELISA (BSA, ovalbumin, phOx-KLH, phOx-CSA, phOx-polylysine, chymotrypsin A, insulin and hen-egg white lysozyme (HEL)), the same antigen concentration was used except for HEL which was coated at 3 mg/ml.

Western Blot Analysis.

SDS-10% polyacrylamide minigels were run with about 10$^{10}$TU of scFV fd phage particles or 1–5 μg of purified scFv. By electroblotting, the proteins were transferred to Immobilon-P membrane (Millipore). The blot was then blocked with PBS 3k BSA for 30 min. For the analysis of cpIII and cpIII-fused scFv, the blot was incubated with rabbit antiserum raised against the cpIII protein followed by mouse anti-rabbit antibody conjugated to horseradish peroxydase (Sigma). Finally, DAB was used as colorimetric substrate for detection. For the detection of biotinylated cpIII-fused scFv by chemisynthesis, streptavidin-alkaline phosphatase was used.

The results obtained are described below.

With the chemisynthetic library described above incorporating cysteine at the CDR3 of the fixed light chain, three different selections against phOx were run in parallel (one negative control library and two semisynthetic libraries). After reduction with DTT, the first library (Lib1;negative control) was modified further whereas the second library (Lib2) was reacted with the alkylating IA-NBD fluorophore and the third (Lib3), with the disulfide exchanger 2-pyridyl-dithio-ethyleneamine reagent (PDEA). Only Lib2 was quenched with DTT after modification with the fluorophore. Four rounds of modification selection-amplification were performed. Between the first and the fourth round, the number of phage particles bound phOx-coated Immuno tubes increased by a factor of 133 for Lib1, 297 for Lib2 and 17 for Lib3.

Figure 1:
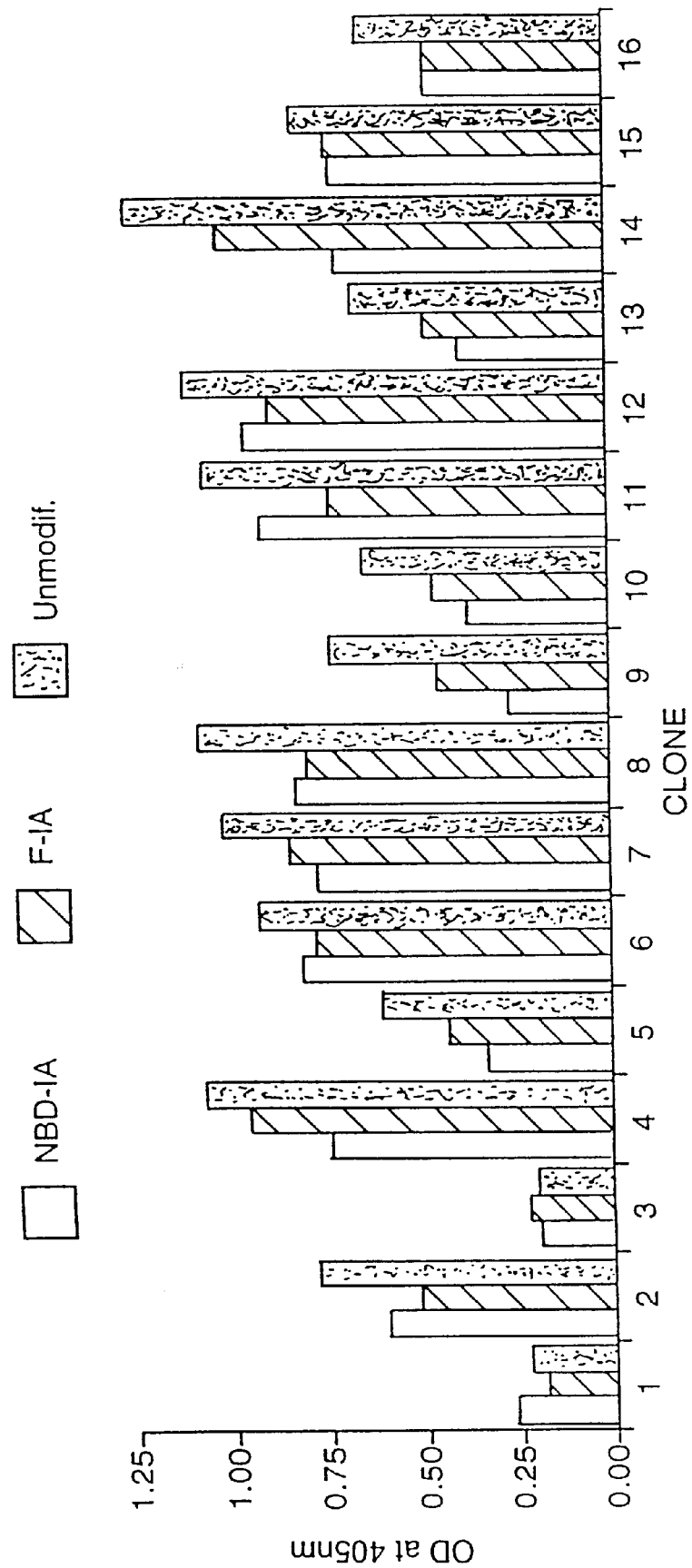
FIG. 1 shows ELISA signals of individual phage from Library 1 which are unmodified or derivatized with NBD-1A or F-IA.

Neither soluble Cys93 scFv nor phage-displayed Cys93 scFv can be efficiently modified in crude culture. supernatant. Therefore, to accelerate the search for antibodies where antigen binding depended on the introduced chemical moiety, polyclonal phage-ELISA were performed with purified phage particles (10 ml cultures) issued from libraries of decreasing size (first, the whole library, then mini-libraries made of 28 to 210 clones). To define the importance of the introduced moiety to the binding activity, negative-control ELISA were done with polyclonal phage particles that were either not modified or modified with another synthetic moiety (usually F-IA). Likewise, individual clones selected from promising mini-libraries (data not shown) were further analyzed by phage-ELISA (FIGS. 1 to 3).

Out of Lib1, sixteen clones (FIG. 1) were analyzed for their binding activity to phOx. Many of them (14/16) gave a positive ELISA signal. As expected, most of unmodified clones bound better to phOx without modification then if they were modified with IA-NBD or IA-F. Two ELISA patterns appeared: a first group (8/14) wherein the clones tolerate chemical modification to a certain extent, and a second group (6/14) of clones which show a stronger preference for not being modified (especially with regard to IA-NBD modification). For example, ELISA signals of IA-NBD modified clones 9 and 14 were about 2.3 times less intense than if the clones were not modified.

Figure 2:
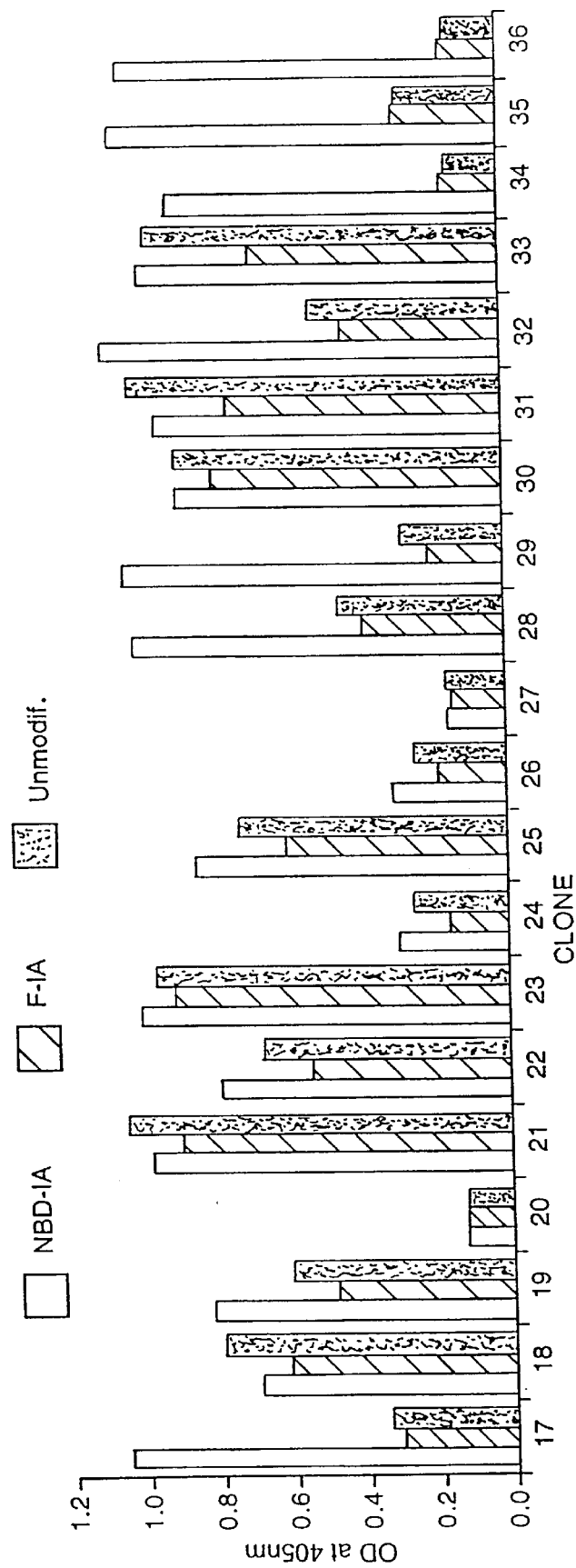
FIG. 2 shows ELISA signals of individual phage from Library 2 which are unmodified or derivatized with NBD-1A or F-IA.

As shown in FIG. 2, twenty clones out of Lib2 were analyzed. Again, a majority of them (16/20) bound to phOx and two groups with interesting binding features were detected. First, a group of clones (9/16) did not show a preference for being modified with IA-NBD. They could bind equally well to phOx as unmodified or IA-F modified phage particles. In the second group (7/16), all IA-NBD-modified clones unveiled a much stronger preference for binding a phOx. This tendency raised from a factor 2.3 times (clone 32) to 6.8 times (clone 36). For the latter, no modification or IA-F modification provoked a drop of ELISA signal down to the background level. Therefore, IA-NBD is part of the antigen binding site.

Figure 3:
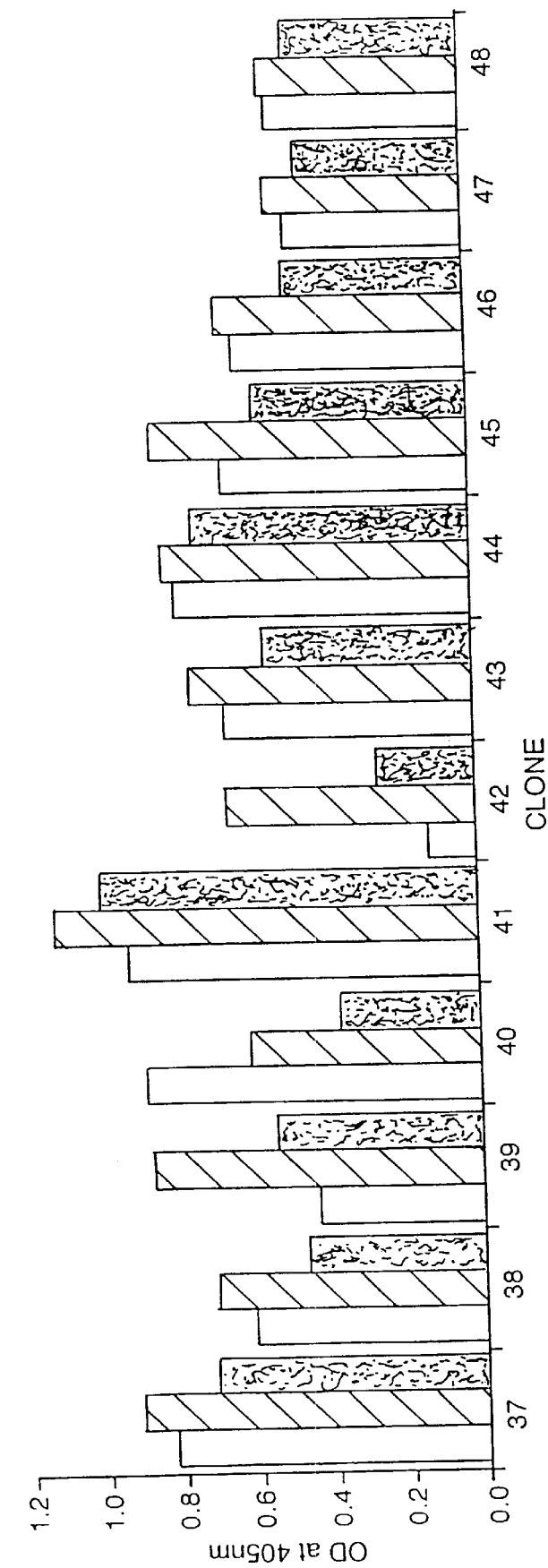
FIG. 3 shows ELISA signals of individual phage from Library 3 which are unmodified or derivatized with NBD-1A or F-IA.

The phage-ELISA signals of twelve Lib3 clones are presented in FIG. 3. Again, the clones could be separated into two groups. The majority of the clones (10,12) first group) showed no marked preference for being modified or not. The second group included only two clones where PDEA affected binding properties: the PDEA modification enhanced their ELISA signals by a maximum factor 3.4 times. The fact that less clones (16%) gave PDEA-dependent ELISA signals in comparison to IA-NBD-dependent clones (43%) can be attributed to the size of the synthetic moieties inserted into the scFv (large for IA-NBD, small for PDEA) than to the reactive groups (alkylation for IA-NBD, disulfide exchange for PDEA).

The ELISA signals of Lib1 and Lib2 clones clearly indicated that, for some clones, the covalently bound synthetic moiety is an integral part of the antigen-binding site. In some antibody clones, the presence of the introduced chemical group is not essential for strong binding of the hapten but in others it is essential for strong binding to occur. Such clones from chemisynthetic repertoires would be particularly valuable when, for example reporter groups are incorporated.

No clone showing a marked ELISA preference for not being modified was found in the two semisynthetic libraries (Lib2 and Lib3).

The semisynthetic library selections thus produced phage antibodies with different binding properties, and different tolerances to modification (Table 1). Individual clones of different ELISA profiles, were selected for DNA sequencing, and the VH-CDR3 sequence, and the VH germline gene determined (Table 1). The VHCDR3 sequences of the clones indifferent to the presence or type of modification display a strong similarity to those obtained from the synthetic repertoire by Hoogenboom & Winter (1992, supra). For example, the VHCDR3 sequences of clone SSL14 from the unmodified library, and clone SSL-41 from the PDEA modified library (LSGVRDFY) are identical to αOx-18 from the original study. Similarly, clones SSL-18 from the NBD modified library and SSL-44 from the PDEA modified library (SMGAKFDY) are almost identical to αOx-1 (SMGSKFDY). In contrast, the clones with the greatest preference for modification, clones SSL-34 (GLLST) from the NBD modified library, and SSL-42 (TRFATDY) from the PDEA selected library, do not share any similarities with the clones from the original study, although the sample size is too small to make any firm conclusions.

Further analysis of the semi-synthetic clones was performed on clones SSL-32 and SSL-34 from the IA-NBD selected library as these clones displayed a marked preference for modification. The clones were of VH3 origin and were purified on protein. A Sepharose from culture supernatant containing soluble scFv fragments. The purified material was modified with IA=NBD, and analyzed by ELISA without the removal of the uncoupled quenched IA-NBD, or the protein was size fractionated by FPLC gel filtration using Superdex 75 to obtain monomeric scFv fragments, free from any uncoupled contaminant. The modification process did not appear to induce any change in the multimerization of the antibody as judged by the FPLC trace of unmodified and modified protein (data not shown).

Figure 4:
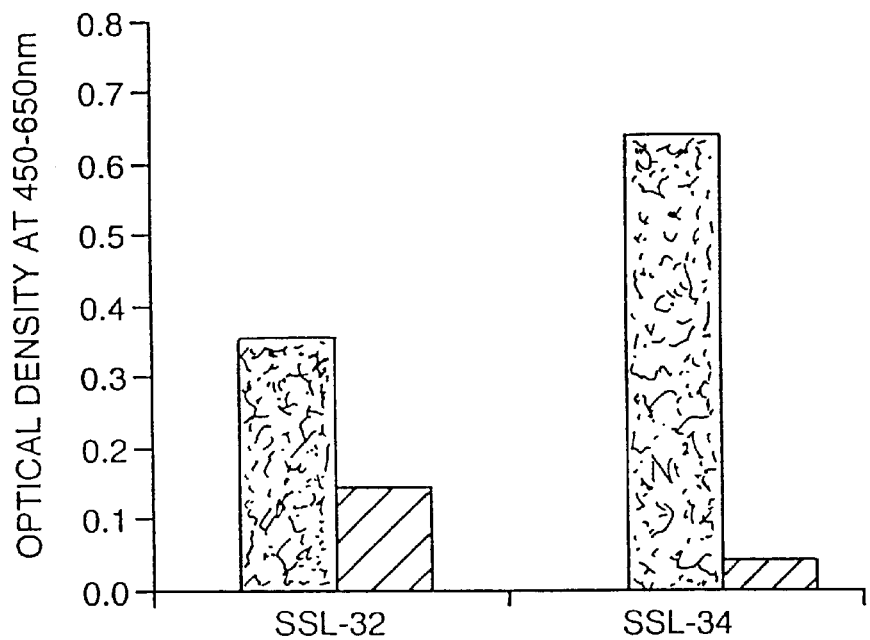
FIG. 4 shows the effect of modification with IA-NBD of soluble scFv fragments on the ELISA signal obtained for the two clones SSL-32 and SSL-34. Soluble single chain Fv fragments were purified by FPLC gel filtration on Superdex 75 to give monomeric fragments and modified with IA-NBD (black bar) or left unmodified (shaded bar).

The binding specificity of the modified and unmodified scFv material was determined by ELISA on microtitre plates coated with phOx-BSA, a number of irrelevant antigens, and a number of other phOx-protein conjugates. The soluble SSL-32 scFv was found to bind to phOx-BSA as an unmodified scFv to a similar extent as the phage antibody, and was not characterized further (FIG. 4). The binding of the SSL-34 clone to phOx-BSA had an absolute requirement for modification with IA-NBD (FIG. 4). Thus, in both cases, the binding characteristics for unmodified and NBD modified fragments mirrored that exhibited for the phage antibody.

The increased ELISA signal for both clones when modified with NBD was not a result of increased multimerizaton, as revealed by FPLC gel filtration analysis.

The absolute requirement of the SSL-34 clone for NBD modification was analyzed in greater detail. No detectable binding was found for the IA-NBD modified clone on any irrelevant antigen, or more significantly, on any other phOx-protein conjugate (FIG. 5). The discrimination for binding of phOx-BSA compared to phoxpoly-L-lysine, phOx-KLH (keyhole limpet haemocyanin) and phOx-CSA (chicken serum albumin) strongly indicates that the NBD modified SSL-34 is recognizing a single phOx derivatized site unique to BSA.

Thus, these results on the creation of a semisynthetic library of antibodies containing non-encoded encoded synthetic moieties as part of the antigen binding site indicate that antibodies with novel antigen binding requirements can be isolated and that the diversity of antibody binding sites can be increased beyond that possible with natural antibodies.

The diversity of the semi-synthetic clones selected here is rather narrow and improvements in the library may be made by inclusion of longer VH-CDR3 sequences, use of different light chains and chemical modification with a population of different cofactors or chemical groups. In addition, the location and number of modifiable (e.g. cysteine) residues is likely to have a significant effect on the properties of the chemisynthetic library and may be varied in a controlled way.

TABLE 1

Sequence and modification tolerance of a subset of chemlsynthetic clones.

| Clone | Library | VH-CDR3 Sequence | Germline Gene | Effect of modification | | |
|-------|---------|------------------|---------------|------|-------------|-----|------|
| | | | | None | Fluorescein | NBD | PDEA |
| SSL-7  | Control | RLPHT    | VH3-DP-46 | +++ | ++  | ++  |     |
| SSL-8  | Control | AESRIFDY | VH3       | +++ | ++  | ++  |     |
| SSL-10 | Control | SIFPPFDY | VH3       | ++  | +   | +   |     |
| SSL-14 | Control | LSGVRFDY | VH3-DP-45 | +++ | +++ | ++  |     |
| SSL-17 | NBD     | RSGIRFDY | VH3-DP-45 | +   | +   | +++ |     |
| SSL-18 | NBD     | SMGAKFDY | VH4-DP-67 | ++  | ++  | ++  |     |
| SSL-32 | NBD     | RRGLTFDY | VH3-DP-45 | +   | +   | +++ |     |
| SSL-34 | NBD     | GLLST    | VH3-DP-53 | –   | –   | +++ |     |
| SSL-38 | PDEA    | RIPHA    | VH3-DP-46 | +   |     | +   | ++  |
| SSL-41 | PDEA    | LSGVRFDY | VH3-DP-45 | +++ |     | +++ | +++ |
| SSL-42 | PDEA    | TRFATFDY | VH1-DP-14 | +   |     | –   | ++  |
| SSL-44 | PDEA    | SMGAKFDY | VH4-DP-67 | ++  |     | ++  | ++  |

Clones were taken from the unmodified library (control) and the libraries modified with IA-NBD (NBD) and PDEA. The deduced synthetic VH-CDR3 sequence and the germline gene is also shown. The effect of and tolerance to modification was determined by ELISA of modified phage antibody particles.
The ELISA signal absorbance produced is represented by + and – symbols: +++ = A > 1.0; ++ = A 0.75–1.0; + = A 0.3–0.75; – = A < 0.3

We claim:

1. A diverse repertoire of first specific binding pair (sbp) members each having a binding site for second sbp member and each being fused to a surface component of a bacteriophage, wherein each first sbp member has a first polypeptide domain which comprises a binding region of immunoglobulin heavy chain variable domain (VH) and a second polypeptide domain which comprises a binding region of an immunoglobulin light chain variable domain (VL), the first and in that each binding site comprises a chemical moiety bound covalently at an amino acid residue within the binding site.

2. A method of providing a diverse repertoire of first specific binding pair (sbp) members each of which has a binding site and is fused to a surface component of a bacteriophage, each first sbp member having a first polypeptide domain which comprises a binding region of an immunoglobulin heavy chain variable domain (VH) and a second polypetide domain which comprises a binding of an immunoglobulin light chain variable domain (VL), the first and second polypeptide domains forming the binding site, the method being characterized by a step of chemical modification of first sbp members in the repertoire to introduce a chemical moiety bound covalently to an amino acid residue in the binding site of each first sbp member.

3. A method according to claim 2 wherein provision of the repertoire of first sbp members before the step of chemical modification comprises expression from a population of nucleic acid molecules collectively encoding the repertoire.

4. A method according to claim 3 wherein provision of the population of nucleic acid molecules comprises a step of mutation of nucleic acid encoding first sbp member, or a polypeptide component part thereof, to introduce a codon encoding the amino acid residue.

5. A method according to claim 2 wherein the amino acid residue is selectively modified in each first sbp member.

6. A method according to claim 2 wherein the population of nucleic acid molecules is provided by joining gene fragments.

7. A method according to claim 2 wherein the chemical modification is performed in vitro.

8. A method according to claim 2 comprising, following said chemical modification, a step of selection of a first sbp member with a binding site able to bind a second sbp member of interest.

9. A method according to claim 8 wherein the selection is by binding with second sbp member of interest.

10. A method according to claim 8 wherein binding of the selected first sbp member to the second sbp member of interest is enhanced compared with binding of that first sbp member without said chemical moiety.

11. A method according to claim 8 wherein binding of the selected first sbp member to the second sbp member of interest is dependent on the presence of the chemical moiety bound covalently at said amino acid.

12. A method according to claim 8 wherein the first sbp members are expressed fused to a surface component of a bacteriophage so that each bacteriophage in a population thereof thereby displays a first sbp member at its surface, each bacteriophage in the population containing a nucleic acid molecule which encodes the first sbp member displayed at its surface.

13. A method according to claim 12 wherein selection of a first sbp member with a binding site able to bind a second sbp member of interest is followed by recovery of a sequence of nucleotides from the bacteriophage which displays the selected first sbp member on its surface.

14. A method according to claim 13 wherein the sequence of nucleotides is used in the production of a first sbp member with a binding site able to bind that second sbp member of interest.

15. A method of providing a genetically diverse repertoire of first specific binding pair (sbp) members each of which has a binding site for complementary second sbp member and is fused to a surface component of a bacteriophage, each first sbp member having a first polypeptide domain which comprises a binding region of an immunoglobulin heavy chain variable domain (VH) and a second polypeptide domain which comprises a binding region of an immunoglobulin light chain variable domain (VL) the first and second polypeptide domains forming the binding site, the method comprising:

provision of a population of nucleic acid molecules collectively encoding a genetically diverse repertoire of first sbp members, the binding site of the encoded first sbp members each having an amino acid residue which is selectively modifiable to introduce a covalently bound chemical moiety into the binding site;

expression from the nucleic acid to provide a repertoire of first sbp members.

16. A method according to claim 15 wherein provision of the population of nucleic acid molecules comprises a step of mutation of nucleic acid encoding first sbp member, or a polypeptide component part thereof, to introduce a codon encoding the amino acid residue.

17. A method according to claim 15 wherein the population of nucleic acid molecules is provided by joining gene fragments.

18. A method according to claim 15 comprising chemical modification of first sbp members in the repertoire thereof at said amino acid residue to introduce a covalently bound chemical moiety into the binding site.

19. A method according to claim 18 comprising, following said chemical modification, a step of selection of first sbp member with a binding site able to bind a second sbp member of interest.

20. A method according to claim 19 wherein the selection is by binding with second sbp member of interest.

21. A method according to claim 19 wherein binding of the selected first sbp member to the second sbp member of interest is enhanced compared with binding of that first sbp member without said chemical moiety.

22. A method according to claim 19 wherein binding of the selected first sbp member to the second sbp member of interest is dependent on the presence of the chemical moiety bound covalently at the amino acid.

23. A method according to claim 19 wherein the first sbp members are expressed fused to a surface component of a bacteriophage so that each bacteriophage in a population thereof thereby displays a first sbp member at its surface, each bacteriophage in the population containing a nucleic acid molecule which encodes the first sbp member displayed at it surface.

24. A method according to claim 23 wherein selection of a first sbp member with a binding site able to bind a second sbp member of interest is followed by recovery of a sequence of nucleotides from the bacteriophage which displays the selected first sbp member on its surface.

25. A method according to claim 24 wherein the sequence of nucleotides is used in the production of a first sbp member with a binding site able to bind that second sbp member of interest.

* * * * *